US00PP26166P2

(12) United States Plant Patent
Kordes

(10) Patent No.: US PP26,166 P2
(45) Date of Patent: Dec. 1, 2015

(54) CLIMBING ROSE PLANT NAMED 'KORHEMTRA'

(50) Latin Name: *Rosa hybrida*
Varietal Denomination: KORhemtra

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 121 days.

(21) Appl. No.: 13/987,681

(22) Filed: Aug. 20, 2013

(51) Int. Cl.
*A01H 5/02* (2006.01)

(52) U.S. Cl.
USPC ..... Plt./110

(58) Field of Classification Search
USPC ..... Plt./110
See application file for complete search history.

(56) References Cited

PUBLICATIONS

CPVO, Feb. 15, 2013, p. 83.*

* cited by examiner

*Primary Examiner* — Keith O. Robinsnon

(57) ABSTRACT

A new and distinct variety of rose with long lasting, novel white flowers, and attractive foliage with excellent disease resistance. It exhibits climbing and arching growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORhemtra'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORhemtra'.

SUMMARY OF THE INVENTION

The new rose plant may be distinguished from its seed parent, an un-named seedling, by the following combination of characteristics:

1. 'KORhemtra' has white flowers, whereas the un-named seedling has soft pink flowers.

2. 'KORhemtra' has excellent disease resistance, whereas the un-named seedling has average disease resistance.

The new rose plant may be distinguished from its pollen parent, an un-named seedling, by the following combination of characteristics:

1. 'KORhemtra' has white flowers, whereas the un-named seedling has red flowers.
2. 'KORhemtra' has a very double petal count, whereas the un-named seedling has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORhemtra' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORhemtra' was selected in May 2003 from the seedling beds to be asexually propagated for further evaluation. The first asexual propagation of 'KORhemtra' was done by budding in July 2003 at the inventor's nursery in Offenseth-Sparrieshoop, Germany.

These initial and other subsequent propagations conducted in controlled environments demonstrate that 'KORhemtra' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORhemtra' taken from a plant of 5 years of age.

DETAILED BOTANICAL DESCRIPTION

The following is a description of 'KORhemtra', as observed growing in June 2013 in a nursery in Jackson County, Oreg. on plants of 5 years of age. Color references are made using The Royal Horticultural Society (London, England) Colour Chart, 2001 except where common terms of color are used.

For a comparison, several physical characteristics of the rose variety 'KORadigel', a rose variety from the same inventor described and illustrated in U.S. Plant Pat. No. 16,936 and issued on Jul. 12, 2006 are compared to 'KORhemtra' in Chart 1.

CHART 1

| Characteristic | 'KORhemtra' | 'KORadigel' |
|---|---|---|
| Flower color, general tonality | White | Pink |
| Fragrance | Light | Strong |
| Disease resistance | Excellent | Very good |

Parents:

*Seed parent*.—An un-named seedling.

*Pollen parent*.—An un-named seedling.

Classification:

*Botanical classification*.—*Rosa hybrida* 'KORhemtra'.

*Commercial classification*.—Climbing rose.

Flower and Flower Bud

Blooming habit: Recurrent.

Flower bud:

*Size*.—Upon opening, 23 mm in length from base of receptacle to distal end of bud and 19 mm diameter at its widest point.

*Bud form*.—Short. Pointed ovoid.

*Bud color*.—As sepals first unfold, bud color is Yellow Group 4D with intonations of Red Group 37C on the tip of the bud. When ¼ open, the upper surface of petals is White Group 155C, and the lower surface is White Group 155C.

*Sepals*.—Color: Upper surface: Yellow-Green Group 147C. Lower surface: Yellow-Green Group 144A. Intonations: Greyed-Purple Group 187B. Size: Average 18-22 mm (l)×7 mm (w). Shape: Weak foliaceous appendages on 3 of the five sepals. Apex: Apiculate. Base: Flat at union with receptacle. Quantity: Five. Surface texture: Upper side: Very pubescent. Lower surface: Stipitate glands present. Stipitate glands: Abundant numbers on lower surfaces and margins.

Flower bloom:

*Fragrance*.—Light.

*Duration*.—On the plant 6 days. Senesced petals drop away cleanly.

*Size*.—Medium for a climbing rose. When open, the average flower diameter is 65-70 mm and the average flower height is 25 mm.

*Form*.—Shape of flower when viewed from the side: Upon opening, upper part: Flattened convex. Upon opening, lower part: Flattened convex. Open flower, upper part: Flattened convex. Open flower, lower part: Concave.

Color:

*Upon opening, petals*.—Outermost petals: Outer Side: White Group 155C. Inner Side: White Group 155C. Innermost petals: Outer Side: White Group N155C. Inner Side: White Group N155D.

*Upon opening, basal petal spots*.—Basal petal spot, outermost petals: Outer Side: Green-White Group 157A. Inner Side: Green-White Group 157A. Basal petal spot, innermost petals: Outer Side: Green-Yellow Group 1D. Inner Side: Green-Yellow Group 1D.

*After opening, petals*.—Outermost petals: Outer Side: White Group 155C. Inner Side: White Group 155C. Innermost petals: Outer Side: White Group 155B. Inner Side: White Group 155B.

*After opening, basal petal spots*.—Basal petal spot, outermost petals: Outer Side: Green-White Group 157A. Inner Side: Green-White Group 157A. Basal petal spot, innermost petals: No distinctive coloration at petal base observed.

General tonality: On open flower White Group 155C. No change in the general tonality until petal drop.

Petals:

*Petal count*.—Very Double.

*Average range*.—Approximately 50 petals under normal conditions.

*Petal reflex*.—Petals reflex somewhat.

*Petal margin*.—Entire.

*Petal shape*.—Obovate. Apex: Obtuse. Base: Cuneate.

*Petal size*.—25-35 mm (l)×18-28 mm (w).

*Thickness*.—Thin.

*Petal arrangement*.—Quartered.

*Texture*.—Upper and Lower Surfaces: Smooth to slightly rugose.

Petaloids:

*Petaloid count*.—Average of 10-12 per flower.

*Petaloid size*.—12-15 mm (l)×5-10 mm (w).

*Petaloid color*.—Inner side: White Group 155B. Outer side: White Group 155B.

*Petaloid texture*.—Inner and Outer Sides: Smooth.

*Margins*.—Entire.

*Petaloid shape*.—Most commonly obovate to spatulate with some petaloids highly irregular. Apex: Obtuse. Base: Attenuate.

Reproductive organs:

*Pistils*.—Few. Approximately 25-30 present. Stigmas: Location: At the same position as anthers. Color: Green-Yellow Group 1C. Styles: Length: 7-8 mm. Color: White Group 155C.

*Stamens*.—Approximately 35-40 on average and regularly arranged. Anthers: Size: Average 3 mm (l)×1.5 mm (w). Color: Greyed-Yellow Group 161D. Pollen: Generally present. Color: Greyed-Orange Group 163C. Filaments: Color: White Group 155D. Length: 7-8 mm.

Receptacle:

*Surface*.—A few fine hairs present.

*Color*.—Green Group 143C. Intonations: Greyed-Purple Group 187C.

*Shape*.—Urn-shaped.

*Texture*.—Smooth.
*Size*.—5 mm (h)×5 mm (w).

Pedicel:
*Surface*.—With abundant stipitate glands.
*Length*.—30-35 mm average length.
*Diameter*.—2 mm average diameter.
*Color*.—Yellow-Green Group 144B.
*Strength*.—Somewhat weak.
*Texture*.—Smooth.
*Borne*.—Multiple flower buds per stem, generally 1 to 5. Flowers pendant.

Peduncle:
*Surface*.—Glabrous.
*Length*.—60-70 mm average length.
*Diameter*.—3 mm average diameter.
*Color*.—Yellow-Green Group 144B.
*Strength*.—Somewhat strong.
*Texture*.—Smooth.

Inflorescence:
*Type*.—Corymb.
*Average number of flowers*.—1 to 5.
*Average size*.—35 cm (w)×25 cm (h).

The Plant

*Growth*.—Moderately vigorous.
*Plant habit*.—Arching. Climbing. When grown as a field plant, the average plant height is 200-240 cm and the average plant width is 80-90 cm.
*Stems*.—Stem color: Young wood: Yellow-Green Group 144B. Older wood: Yellow-Green Group 144A. Stem surface texture: Young wood: Smooth. Older wood: Rough.
*Prickles*.—Present. Incidence: Average of 6-8 per each 10 cm of stem. Size: Average length: 7-9 mm. Color: Immature prickles: Greyed-Yellow Group 162D. Mature prickles: Greyed-Yellow Group 162D. Senescing to Greyed-Yellow Group 160D. Intonations: Greyed-Orange Group 166B covering most of the juvenile prickles. Shape: Deeply concave. Texture: Smooth.
*Leaves*.—Normally 7 leaflets on normal leaves in middle of the stem. Venation pattern: Pyramidal net pattern. Leaf size: 175-185 mm (l)×105-115 mm (w). Abundance: Average. Texture: Upper side of leaf: Smooth. Under side of leaf: Smooth.
*Leaflets*.—Size: Average size of the terminal leaflet is 50-60 mm (l)×38-40 mm (w). Shape: Elliptic. Base: Obtuse. Apex: Acute. Margins: Serrated. Surface: Upper side of leaflet: Semi-glossy. Lower side of leaflet: Matte. Texture: Upper side of leaflet: Smooth. Under side of leaflet: Smooth. Color, mature foliage: Upper Leaflet Surface: Green Group 137A. Lower Leaflet Surface: Green Group 138B. Color, juvenile foliage: Upper Leaflet Surface: Green Group 137A. Lower Leaflet Surface: Green Group 138B. Arrangement: Odd pinnate. Venation: Reticulate.
*Stipules*.—Size: 30-40 mm (l)×10-15 mm (w). Stipule color: Green Group 137C. Stipitate glands: Abundant number along margins. Texture: Smooth. Shape: Apex: Aristate. Base: Flat.
*Petiole*.—Length: Average 20-25 mm. Diameter: Average 1 mm. Petiole color: Yellow-Green Group 144A. Underneath: Yellow-Green Group 144B. Margins: With limited numbers of stipitate glands. Prickles: A few small prickles underneath. Texture: Smooth.
*Petiole rachis*.—Length: Average 75 mm. Diameter: Average 1.5 mm. Color: Yellow-Green Group 144A. Margins: With limited numbers of stipitate glands. Prickles: A few small prickles underneath. Texture: Smooth.

Hips/seed formation: None observed.

Winter hardiness: To date, the variety has been grown successfully in Zone 6.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

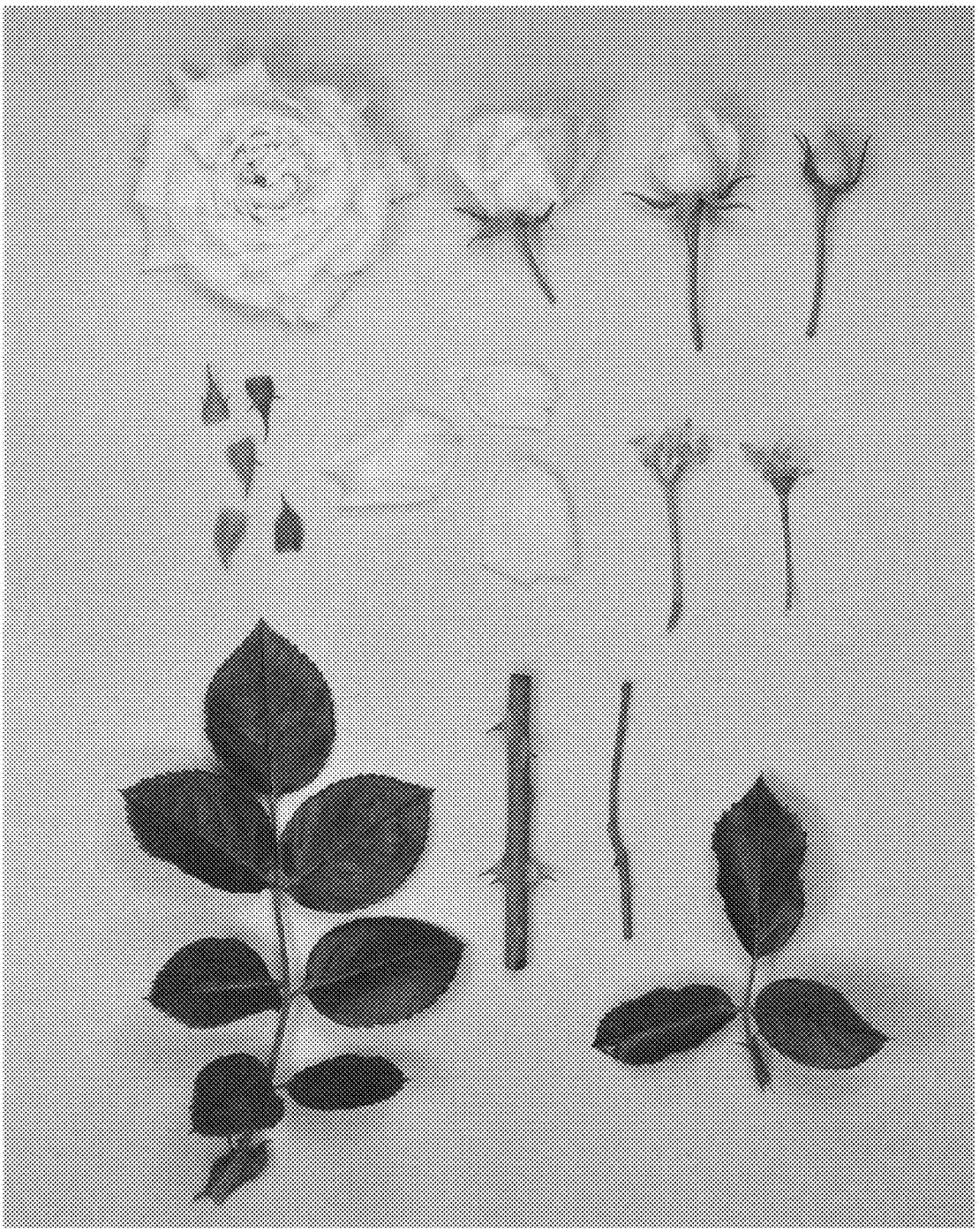

* * * * *